US011659991B2

(12) United States Patent
Lubatschowski (10) Patent No.: US 11,659,991 B2
(45) Date of Patent: May 30, 2023

(54) OCT IMAGE CAPTURE DEVICE

(71) Applicant: ROWIAK GMBH, Hannover (DE)

(72) Inventor: Holger Lubatschowski, Hannover (DE)

(73) Assignee: OCUMAX HEALTHCARE GMBH, Hannover (DE)

( * ) Notice: Subject to any disclaimer, the term of this patent is extended or adjusted under 35 U.S.C. 154(b) by 654 days.

(21) Appl. No.: 16/606,040

(22) PCT Filed: Apr. 18, 2018

(86) PCT No.: PCT/EP2018/059929
§ 371 (c)(1),
(2) Date: Oct. 17, 2019

(87) PCT Pub. No.: WO2018/192988
PCT Pub. Date: Oct. 25, 2018

(65) Prior Publication Data
US 2021/0145273 A1 May 20, 2021

(30) Foreign Application Priority Data

Apr. 18, 2017 (DE) .......................... 102017108193.3

(51) Int. Cl.
*G01B 9/02* (2022.01)
*A61B 3/10* (2006.01)
*G01B 9/02091* (2022.01)

(52) U.S. Cl.
CPC .......... *A61B 3/102* (2013.01); *G01B 9/02041* (2013.01); *G01B 9/02091* (2013.01)

(58) Field of Classification Search
CPC ................ A61B 3/102; G01B 9/02041; G01B 9/02091; G01B 9/02029; G01B 9/0203; G01B 9/02057; G01B 9/02087
See application file for complete search history.

(56) References Cited

U.S. PATENT DOCUMENTS

| 8,126,534 B2 | 2/2012 | Maschke |
| 2007/0123761 A1 | 5/2007 | Daly et al. |
| 2009/0149739 A9 | 6/2009 | Maschke |

(Continued)

FOREIGN PATENT DOCUMENTS

| CN | 10179212 A | 8/2010 |
| CN | 101866482 | 10/2010 |

(Continued)

OTHER PUBLICATIONS

Holtmann, Ch.; Besse, P.-A.; Melchior, H.: 'High power superluminescent diodes for 1.3 μm wavelengths', Electronics Letters, 1996, 32, (18), p. 1705-1706, DOI: 10.1049/el:19961117 (Year: 1996).*

(Continued)

*Primary Examiner* — Tarifur R Chowdhury
*Assistant Examiner* — Jonathon Cook
(74) *Attorney, Agent, or Firm* — Price Heneveld LLP (57) ABSTRACT

An OCT examination device for recording an object comprises an OCT radiation source which emits OCT radiation, an OCT beam path, a housing, an exit opening formed in the housing for the OCT radiation of the OCT radiation source, an OCT exit direction of the radiation through the exit opening, a control unit connected to the OCT radiation source OCT radiation and configured to record a multiplicity of measurement profiles mutually separated in a recording period and, within the recording period, to drive the OCT radiation source in order to emit the OCT radiation and the OCT radiation receiver in order to receive the backscattered OCT radiation, and to keep an OCT output direction and an OCT exit direction constant with respect to one another in their angular orientation during the recording period.

20 Claims, 5 Drawing Sheets

(56) References Cited

U.S. PATENT DOCUMENTS

| | | | |
|---|---|---|---|
| 2011/0181702 A1* | 7/2011 | Hauger | G01B 9/02091 |
| | | | 348/46 |
| 2012/0320179 A1* | 12/2012 | Im | A61B 6/463 |
| | | | 348/E7.085 |
| 2014/0160264 A1 | 6/2014 | Taylor et al. | |
| 2014/0285812 A1 | 9/2014 | Levitz | |
| 2015/0133778 A1 | 5/2015 | Rivera et al. | |
| 2017/0027438 A1 | 2/2017 | Uhlhorn et al. | |
| 2017/0035287 A1 | 2/2017 | Ren et al. | |
| 2017/0105618 A1* | 4/2017 | Schmoll | G01B 9/02043 |
| 2017/0280989 A1* | 10/2017 | Heeren | A61B 5/684 |

FOREIGN PATENT DOCUMENTS

| | | |
|---|---|---|
| CN | 103148778 | 6/2013 |
| CN | 103392191 | 11/2013 |
| CN | 103959040 | 7/2014 |
| CN | 104114080 | 10/2014 |
| CN | 105917358 | 8/2016 |
| CN | 106455978 | 2/2017 |
| DE | 10343808 | 5/2005 |
| DE | 102009022958 | 12/2010 |
| WO | 2009131679 | 10/2009 |
| WO | 2013027173 | 2/2013 |
| WO | 2015189174 | 12/2015 |

OTHER PUBLICATIONS

Andrei B. Vakhtin et al, "Common-path interferometer for frequency-domain optical coherence tomography," Applied Optics, Bd. 42, nr. 34, Dec. 1, 2003, Washington, DC (Abstract only).

* cited by examiner

OCT IMAGE CAPTURE DEVICE

CROSS-REFERENCE TO FOREIGN PRIORITY APPLICATION

The present application claims the benefit under 35 U.S.C. §§ 119(b), 119(e), 120, and/or 365(c) International Application PCT/EP2018/059929 filed Apr. 18, 2018, which claims priority to German Application No. 102017108193.3 filed Apr. 18, 2017.

FIELD OF THE INVENTION

The invention relates to an OCT examination device for recording an object by means of optical coherence tomography, comprising an OCT radiation source, which emits OCT radiation with a wavelength of from 400 nm to 2000 nm and a spectral bandwidth that comprises at least a range of from 20 nm to 400 nm, or has a narrow bandwidth of less than 20 nm to 400 nm, the radiation source being tunable in such a way that the narrow bandwidth forms a wider bandwidth of from 20 nm to 400 nm by time-offset emission of waves at different wavelengths, an OCT beam path, comprising an OCT output direction of the OCT radiation from the OCT radiation source, and an OCT input direction of OCT radiation scattered back by an image object, an OCT radiation receiver for receiving the backscattered OCT radiation of the OCT radiation source, a housing, which contains the OCT radiation source and the OCT radiation receiver, an exit opening formed in the housing for the OCT radiation of the OCT radiation source, an entry opening formed in the housing for the backscattered OCT radiation of the OCT radiation source, an OCT exit direction of the radiation through the exit opening, an OCT entry direction of the backscattered OCT radiation through the entry opening, a control unit, which is connected in terms of signal technology to the OCT radiation source and the OCT radiation receiver and is configured in order to record a multiplicity of measurement profiles mutually separated in a recording period and, within the recording period, to drive the OCT radiation source in order to emit the OCT radiation and the OCT radiation receiver in order to receive the backscattered OCT radiation.

BACKGROUND OF THE INVENTION

Optical coherence tomography (OCT) is an examination method in which light with a short coherence length is used with the aid of an interferometer for distance measurement in scattering materials. The OCT examination method is used, for example, in medicine for examination in vivo and in vitro. This medical application is also applied in other fields outside medicine in order to examine scattering materials. In principle, it is to be understood that the OCT diagnosis device according to the invention and the method according to the invention for OCT image capture of an object may be used as diagnostic methods which are carried out on the human or animal body, but may also be used as analysis methods for a different purpose, i.e., with the exclusion of those diagnostic methods which may be carried out on the human or animal body. OCT examination methods are distinguished in that the examined material is not modified by the OCT examination process and, therefore, have neither a surgical nor a therapeutic effect. It is to be understood that the claimed method for the OCT image capture of an object is the subject-matter of this description and the claims in territories which exclude diagnostic methods on human bodies from patent protection, with the exclusion of the protection of such diagnostic methods on the human body.

OCT systems are measuring systems which, by aligning a measurement beam with an area, to be considered in an idealized way as a point, of the object to be examined, carry out a point measurement on this object on the basis of the backscattered radiation. In order to image the object surface and the depth region lying immediately below it, with a typical penetration depth of from 1 to 3 mm, over a sizeable surface region or as a whole, OCT measuring systems must, therefore, move the measurement beam over the surface by scanning, which is typically carried out as a line scanning. This scanning is achieved in OCT measuring systems by motor-driven deflecting mirrors. High-quality OCT image capture is, therefore, carried out by fixing the object to be examined, arranging the OCT measuring device in a fixed position with respect to the object, and then scanning the surface of the object by automatically performed scanning by means of the deflecting mirror, so as to obtain a representation of the surface and of the region lying immediately below the surface by a multiplicity of single-point measurements.

This measurement method has generally been tried and tested, achieves reliable imaging qualities, and may be carried out with a fast measurement. A disadvantage, however, is that fixing the object to be examined is necessary in order to avoid a relative movement between the object and the OCT measuring device over the scanning period. This fixing is disadvantageous, particularly when using the OCT measuring device for diagnostic purposes, for example, in order to examine the retina of the human eye, since the outlay required therefor in order to fix the head or the eye is considerable.

An operation microscope having an OCT examination device coupled in is known from US 2017/0027438. The OCT measurement beam is in this case coupled into the beam path of the microscope by means of two mobile mirrors and a stationary mirror, and is consequently deflected three times. The guide beam paths of the OCT beam are intended to remain substantially parallel to the optical axis of the microscope 100 by the doubly control led deflection, in order to avoid image distortions. The technology previously known to this extent is not suitable for keeping the angle between the output direction of an OCT beam from the OCT source and the exit direction of the OCT beam from the housing constant, but can only achieve this angle being substantially constant. Such a configuration, in which the angle cannot, however, actually be kept parallel to the axis of the microscope because of the double deflection and the principle of scanning the examination region by means of the double deflection, is not to be understood in the sense according to the invention that the angle between the output direction of the OCT beam from the OCT source and the exit direction of the OCT beam from the housing is kept constant thereby. The device thus previously known captures the examination region by means of the OCT device by a scanning process, and, therefore, requires fixing of the device in relation to the object to be examined. Furthermore, the device occupies considerable installation space and is therefore unwieldy to use in narrow spatial situations.

There is, therefore, a need for an OCT examination device which, for carrying out the OCT examination, is simplified overall and is less sensitive to measurement errors that occur because of a relative movement between the OCT measuring device and the object to be examined.

SUMMARY OF THE INVENTION

This object is achieved with an OCT examination device of the type mentioned in the introduction, in that the control unit is configured in order to keep the OCT output direction and the OCT exit direction constant with respect to one another in their angular orientation during the recording period. According to the invention, the image capture is carried out by scanning the surface of the object to be examined with a measurement beam in the case of the OCT examination device. This image capture is carried out during a recording period which starts with the recording of the first measurement point in the scan and ends with the recording of the last measurement point in the scan. Within this recording period, a plurality of, i.e., at least two and, in general, a few hundred or thousand, measurement points are thus addressed with the measurement beam and the surface is thereby scanned, for example, in lines or spirally.

While this scan is carried out in the prior art in an automated manner by a motor-adjustable deflecting mirror or other beam deflecting devices, so that the OCT output direction of the beam from the OCT radiation source is variable in terms of its angular orientation relative to the OCT exit direction of the measurement beam from the OCT examination device, and is varied during the recording period in order to carry out the scanning, in the case of the OCT examination device according to the invention the angular orientation of the OCT output direction and of the OCT exit direction are kept constant during the entire recording period. The OCT examination device according to the invention can, therefore, obviate an adjustment, carried out in a motorized or other fashion, of this angular orientation between the OCT output direction and the OCT exit direction, and, in particular, also an adjustable deflecting mirror, which has the further advantage that the OCT examination device according to the invention may be configured more compactly than previously known OCT examination devices. Instead of the motorized adjustments of a deflecting mirror or a correspondingly differently constructed variable beam deflecting device according to the prior art, the compact configuration of the OCT device makes it possible to carry out the scan of the object surface to be examined by a movement of the OCT examination device relative to the object to be examined. The relative movement may be carried out as a displacement or tilt, or a combination thereof, of the OCT examination device itself, although the object to be examined may also be displaced or tilted with the OCT examination device kept spatially stationary, in order to produce the relative movement which is required for the scan.

In the OCT examination device according to the invention, the OCT measurement beam is directed through an exit opening onto the object to be examined, and the backscattered OCT radiation re-enters the OCT examination device through an entry opening. In principle, it is to be understood that although two separate openings may be provided in particular applications, it is particularly preferred for the entry opening and the exit opening to be formed by a single housing opening. In particular, the OCT radiation coming from the single opening, i.e., the measurement beam and the backscattered OCT radiation, may extend coaxially, which makes the OCT examination device insensitive to different measurement distances between the entry/exit opening and the surface to be examined.

According to another preferred embodiment, the exit opening and the OCT radiation source are arranged in such a way that the OCT exit direction and the OCT output direction extend parallel to one another, in particular, coaxially. According to this embodiment, the radiation emerging from the OCT radiation source may be oriented directly in the direction of the exit opening and no longer needs to be deflected in order to pass from the OCT radiation source through the exit opening. This embodiment is suitable, in particular, for a slim design of the housing, for example, in the form of an elongate tubular housing, which allows particularly user-friendly handling of the OCT examination device.

According to another preferred embodiment, the OCT examination device is refined by an observation instrument comprising an illumination radiation source, which emits light in the visible or infrared observation wave range into an illumination beam path passing through the exit opening, and an observation image sensor, which is sensitive to radiation in the observation wave range and which receives reflected light in the visible or infrared observation wave range from an observation beam path passing through the entry opening, the observation beam path and the OCT exit direction extending parallel to one another, in particular, coaxially. Such an observation instrument allows a user to observe the examined object simultaneously with the OCT image capture by sampling with another examination method, which images the surface with light in the visible or infrared range. This observation instrument, on the one hand, makes it possible to carry out a simultaneous examination by means of two different imaging methods, and on the other hand by means of the observation instrument the alignment of the OCT measurement beam with the object to be measured may be monitored while carrying out the OCT examination, and the OCT measurement beam may be aligned with the aid of the image recorded by the observation instrument. In particular, the position of the measurement beam in an image which is recorded by means of the observation instrument may be marked. While in the absence of an observation instrument the user would have to carry out the scan of the object to be examined without a direct position check, this may be carried out in a controlled way in the presence of an observation instrument and the control unit may, in particular, be configured in order to overlay the alignment of the measurement beam of the OCT exit direction and the previous scan points of this measurement beam, i.e., the profile of the scan, into an image which has been compiled by means of the observation instrument.

The scan of the examination object is carried out according to the invention by a relative movement between the OCT examination device and the object to be examined. In contrast to the prior art, it is, therefore, not necessary for the object to be examined and the OCT examination device to be constant, or invariant, in their position with respect to one another during the recording period and for the scan to be carried out by a varying internal deflection or deviation of the OCT measurement beam inside the OCT examination device, but rather the scan and, therefore, the relative movement of the OCT measurement beam is carried out by a relative movement between the OCT radiation source and the object to be examined. This relative movement may, in particular, be carried out manually by a user who guides the OCT examination device by hand. In principle, in a simplified form, this may be carried out in such a way that the user carries out a scan movement manually and without a visual check, relying on the fact that such a line-by-line scan can be carried out reliably in a motorized fashion. The manual scan may, however, also be assisted or guided by a visual check, for example, by a movement direction indicator being displayed to the user on a screen, which indicates the scan direction which the user should carry out manually by displaying an arrow or the like, or by the regions already recorded with the OCT measurement beam being displayed to the user by corresponding reproduction of the OCT examination image, so that the recorded surface of the object to be examined is built up simultaneously with the scan according to the scan movement which the user is carrying out manually. This allows the user to check and correct the scan path which the user is carrying out manually with the aid of the OCT examination image being built up in real-time, or with a time delay, and thereby manually carry out a scan guided spirally or in lines or in another geometrical shape.

In this case, the OCT examination device may furthermore be refined in that the electronic control unit comprises an image processing unit, which is configured in order to combine a first image, formed by the reflected light received by the observation image sensor, and a second image, adjacent to the first image and formed with a time offset with respect to this first image from the reflected light received by the observation image sensor, in order to form an overall image. This configuration of the electronic control unit makes it possible from the scan movement, the recording resulting from the relative movement between the OCT examination device, or the OCT radiation source, and the examined object, recording of a plurality of images with a time offset with respect to one another during the recording period to compile an overall image of the scanned surface of the examined object. This combination may be carried out by joining the individual images together, overlapping regions with identical image contents correspondingly being arranged in an overlapping manner, or these image contents being taken from only one of the two joined images, in order to achieve a unique and gap-free compilation of the overall image. The electronic control unit may, in particular, be configured in order to combine a plurality of images to form an overall image. Furthermore, the electronic control unit may be configured in order to mark the regions recorded with the OCT measurement beam inside these images. Furthermore, the electronic control unit may be configured in order, with the aid of the composed images of the observation instrument, also to combine the image values determined with the OCT measurement beam to form an overall OCT image. This may, in particular, be carried out in such a way that with the aid of the positioning, established by overlap, of the images of the observation instrument with respect to one another, the placement of the individual OCT measurement points with respect to one another is determined and these are assigned to one another in their placement.

Furthermore, it is also preferred for the image processing unit to be configured in order to identify an intersection region of the first and second images, in which a matching image section is reproduced in the first and second images, and to combine the first and second images in such a way that the overall image is composed of the first and second image with an overlap of the first and second images in the matching image section. With the aid of the matching image regions thus established by the control unit, unique assignment of the placement of the two images to be joined in their relation to one another may be carried out, and a gap-free overall image may, therefore, be compiled. In particular, the identification of matching image contents into two or more different images allows unique assignment of OCT measurement points in the respective images, so that a unique assignment of the placement of these OCT measurement points may also be carried out on the basis of such an established overlap.

Furthermore, provision may in this case be made that the image processing unit is configured in order to rectify the first and/or the second image, in particular, by the first and/or the second image being tilted about an image surface normal as a tilt axis, and/or the first and/or the second image being scaled, in particular, being scaled in all regions with a matching scaling factor or with a scaling factor decreasing in one or two mutually perpendicular spatial directions. According to this refinement, the image processing unit is configured in order, in the course of the identification of matching image sections, to carry out rectification which may consist in tilting or scaling, or both. In this case, scaling is also to be understood as scaling in only one axial direction, i.e., scaling which does not keep the side length ratios of the image constant, but changes them. By such scaling or tilting of the image, different recording directions and different recording scales, as well as composite distortion effects resulting therefrom, may be compensated for and two adjacent images which have a different recording angle or recording scale because of such distortion effects may be combined without these distortions occurring as errors in the overall image. In particular, the control unit may be configured in order to carry out a comparison of two images in the check for matching image components, which takes such distortion effects into account by rectification of the images taking place and the comparative analysis of the images over matching image sections being carried out on the basis of the rectified images.

Furthermore, it is also preferred for the control unit to be configured in order to process a measurement profile, compiled from the backscattered OCT radiation received by the OCT radiation receiver, and an image recorded simultaneously from the light received by the observation image sensor, and to mark a region in the image which represents the position of the measurement profile. By the simultaneous processing of the backscattered OCT radiation and of the measurement profile compiled therefrom and of the light received by the observation image sensor, a spatially unique assignment of the OCT measurement profile in relation to the image recorded by the observation image sensor is possible, and sequencing of the individual OCT measurement points in the spatially correct placement with respect to one another may as a result be carried out with the aid of the images recorded by the observation image sensor.

According to another preferred embodiment, the OCT radiation source and the OCT radiation receiver are arranged immovably in the housing. By such an immobile arrangement on the one hand a robust configuration of the OCT examination device is achieved, and furthermore, because of this spatially immobile arrangement, the OCT examination device may be constructed compactly and fitted in a slim housing.

Furthermore, it is also preferred for the OCT beam path to extend immovably in the housing. By such an immobile profile of the OCT beam path, which comprises both the emitted OCT radiation from the OCT radiation source as far as the exit opening in the housing and also the received backscattered OCT radiation from the entry opening as far as the OCT radiation receiver, according to the invention any mobile or controllable deflecting means for the OCT radiation inside the examination device are obviated, which overall makes a robust and slim construction of the OCT examination device possible. Furthermore, it is also preferred for the OCT beam path to be static in relation to the illumination beam path and the observation beam path. By such a static, i.e., immobile relative to one another, arrangement of the OCT beam path with respect to the observation and illumination beam paths, according to the invention a clear assignment, already established by the structure of the OCT examination device, of the orientation of the OCT measurement beam and of the thereby defined position of the OCT measurement point is achieved in the image obtained by the observation device.

Furthermore, it is also preferred to refine the OCT examination device by a placement recording unit, which is configured in order to determine the placement, in particular, the position and/or the orientation of the OCT radiation receiver in relation to a static reference coordinate system, and an image processing unit, which is coupled in terms of signal technology to the placement recording unit and is configured in order to determine a first measurement profile of the backscattered OCT radiation received by the OCT radiation receiver at a first instant, to determine a first placement of the OCT radiation receiver at the instant of receiving of the backscattered OCT radiation of the first measurement profile from placement data which have been transmitted from the placement recording unit at the first instant to the image processing unit, to determine a second measurement profile, adjacent to the first measurement profile, with a time offset with respect to this first measurement profile from the backscattered OCT radiation received by the OCT radiation receiver at a second instant, to determine a second placement of the OCT radiation receiver at the instant of receiving of the backscattered OCT radiation of the second measurement profile from placement data which have been transmitted from the placement recording unit at the second instant to the image processing unit, to determine the relative placement of the first measurement profile with respect to the second measurement profile with the aid of the first and second placements, and to combine the first and second measurement profiles to form an overall measurement profile by entering the first and second measurement profiles into the overall measurement profile at the previously determined relative placement.

According to this embodiment, the OCT examination device furthermore comprises a placement recording unit. This placement recording unit is configured in order to determine a placement of the OCT examination device. This placement determination may be carried out by the placement recording unit in such a way that a relative change in the placement of the OCT examination device takes place between a first and a second instant, for example, by an acceleration of the OCT examination device or accelerations of the OCT examination device along a plurality of axes being recorded by one or corresponding more acceleration sensors, which are a component of the placement recording unit. The placement recording unit may, as an alternative or in addition, also comprise sensors or a sensor which record(s) orientation of the OCT examination device in relation to the direction of the force of gravity, so as to record an absolute placement orientation of the OCT examination device. The placement recording instrument may furthermore contain one or more gyroscopes as sensors, in order to register displacements or tilts along a plurality of axes.

The placement recording instrument may be configured in such a way that it records the placement of the OCT examination device in relation to a reference system which is separate from the OCT examination device and is installed statically in the environment, or a correspondingly statically installed reference point.

By the placement recording of the OCT examination device, on the one hand the placement, i.e., the position and orientation, of the OCT examination device at the instant of an image capture may be determined, and consequently with the aid of the thus determined placement of the OCT examination device joining of a plurality of images or OCT measurement profiles recorded at time intervals and while changing the position of the OCT examination device may be carried out. This may on the one hand be carried out with the aid of absolutely determined placements of the OCT examination device, but as an alternative or in addition also with the aid of relative placement changes of the OCT examination device between two images, or OCT measurement points, recorded with a time offset. It is to be understood that this joining of OCT measurement profiles to form an overall measurement profile may be carried out merely with the aid of the data of the placement recording unit, although the data of the placement recording unit may also be used in addition to another procedure for joining the individual measurement profiles to form an overall measurement profile, for example, by the data of the placement recording unit in addition to joining the measurement profiles with the aid of the images recorded by the observation instrument, determination of their overlap and the thus defined placement of the individual OCT measurement profiles with respect to one another being carried out.

Another aspect of the invention is a method for OCT image capture of an object by means of optical coherence tomography, having the steps: emitting OCT radiation with a wavelength of from 400 nm to 2000 nm and a spectral bandwidth that comprises at least a range of from 20 nm to 400 nm, or has a narrow bandwidth of less than 20 nm to 400 nm, the radiation source being tunable in such a way that the narrow bandwidth forms a wider bandwidth of from 20 nm to 400 nm by time-offset emission of waves at different wavelengths, from an OCT radiation source into an OCT beam, comprising an OCT output direction of the OCT radiation from the radiation source, and an OCT input direction of OCT radiation scattered back by an image object, receiving the backscattered OCT radiation of the OCT radiation source in an OCT radiation receiver, a housing, which has an exit opening and an entry opening for the OCT beam path, containing the OCT radiation source, the OCT radiation receiver, guiding the OCT radiation through the exit opening in an OCT exit direction, guiding the backscattered OCT radiation through the entry opening in an OCT entry direction, driving the OCT radiation source and the OCT radiation receiver by means of a control unit in order to emit the OCT radiation by means of the OCT radiation source and in order to receive the the backscattered OCT radiation by means of the OCT radiation receiver over a recording period, recording a plurality of mutually separated measurement profiles from the backscattered OCT radiation during the recording period, wherein the OCT output direction and the OCT exit direction are kept constant with respect to one another in their angular orientation during the recording period.

The OCT image capture method according to the invention is distinguished in that, during the image recording in which a plurality of OCT measurement points are addressed and a plurality of OCT measurement profiles are correspondingly recorded, no change takes place between the output direction of the OCT radiation from the OCT radiation source and the exit direction of the OCT radiation from the OCT examination device. As explained in the introduction, the method for the OCT image capture of an object may be carried out for any OCT examinations of objects, the method may optionally be carried out with the exclusion of use as a diagnostic method for human or animal bodies.

The method may be refined in that, between the recording of the first and recording of the second image, the observation image sensor is moved, in particular, displaced and/or tilted relative to the image object. The relative movement between the observation image sensor and the image object to be examined may in this case either be carried out by the observation image sensor being moved, in particular, with the entire OCT examination device in which the observation image sensor is arranged being moved, with the object to be examined being stationary, or by the object to be examined being moved with the observation image sensor being fixed. In principle, the relative movement may also be carried out by a movement both of the observation image sensor and of the object to be examined.

According to another preferred embodiment, a first measurement profile and a second measurement profile are recorded within the recording period, and the first and second measurement profiles are assigned to one another in their spatial placement and combined to form an overall measurement profile, in particular, by simultaneously with the recording of the first measurement profile, a first image being recorded by means of emitting light radiation in the visible or infrared wavelength range and receiving the light reflected by an object, simultaneously with the recording of the second measurement profile, a second image being recorded by means of emitting light radiation in the visible or infrared wavelength range and receiving the light reflected by the object, the position of the first measurement profile in the first image being marked, the position of the second measurement profile in the second image being marked, the first and second images being combined with the aid of image analysis to form an overall image by a matching image region of the first and second images being arranged in an overlapping manner, and the relative positioning of the first measurement profile with respect to the second measurement profile being determined with the aid of their position in the overall image, and the first and second measurement profiles being combined with the aid of the relative positioning determined in this way to form an overall measurement profile, or by a first placement of the housing being recorded simultaneously with the recording of the first measurement profile, a second placement of the housing being recorded simultaneously with the recording of the second measurement profile, the relative positioning of the first measurement profile with respect to the second measurement profile being determined with the aid of a relative change in the first placement with respect to the second placement of the housing, and the first and second measurement profiles being combined with the aid of the relative positioning determined in this way to form an overall measurement profile.

According to this embodiment, a plurality of measurement profiles are combined to form an overall measurement profile, and in this way a corresponding OCT examination representation of an examined surface of the object and of an underlying near-surface volume region below this examined surface is generated. The joining of the individual measurement profiles obtained by the scan to form the overall measurement profile may in this case be carried out with the aid of an image analysis with determination of matching image contents and corresponding joining of the individual images to form an overall image ("stitching") or with the aid of a placement determination of the placement of the housing of the OCT examination device and correspondingly of the placement of the OCT measurement beam which emerges from this housing, or a combination of these two methods may be carried out in to join individual measurement profiles form an overall measurement profile.

BRIEF DESCRIPTION OF THE DRAWINGS

The implementation and advantages of the invention may be found from the following descriptions of the Figures. Various exemplary embodiments of the present invention are represented in the figures. The Figures, the description and the claims contain numerous features which have a function individually or in combination. It is to be understood that all features are expediently both to be considered individually and to be understood together in further appropriate combinations.

DETAILED DESCRIPTION OF THE EMBODIMENTS

Figure 1:
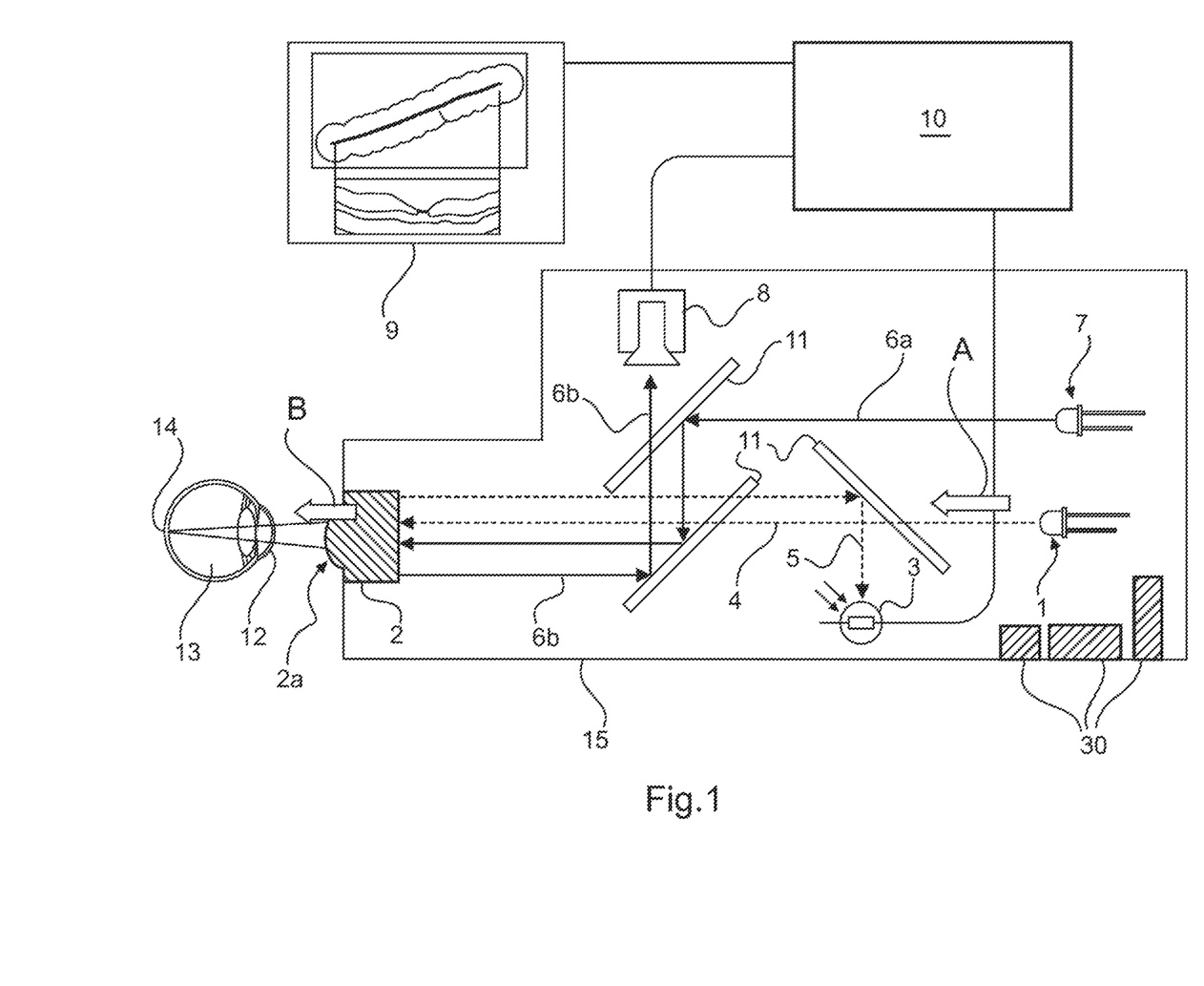
FIG. 1 is a schematic view of the structure of the OCT device according to the invention (for the sake of better representability, the OCT device is represented larger in proportions than an eye to be measured)

The OCT device 15 for achieving the object comprises a short-coherence radiation source (for example SLD) 1 which is distinguished by a corresponding wavelength (400 nm-2000 nm) and spectral bandwidth (20 nm-400 nm) for carrying out optical coherence tomography (OCT). The OCT device 15 furthermore comprises optics 2, with which the measurement beam 4 leaves collimated in the direction of the object to be measured.

From the radiation source, the OCT radiation emerges in an OCT output direction A and strikes the optics. The OCT radiation passes through the optics 2 and emerges in an exit direction B from an exit opening 2a.

Optionally, instead of the broadband light source, a rapidly tunable light source (so called swept source) with a smaller bandwidth may be used.

The arrangement furthermore contains an OCT detector 3 for recording the backscattered OCT radiation 5 of the measurement beam. In the case of the broadband light source, the OCT detector 3 may be a spectrometer which displays the backscattered OCT radiation spectrally decomposed on a linear sensor array (Fourier domain OCT). In the case of the tunable OCT radiation source, the OCT detector 3 may consist of a simple point light sensor (photodiode) (swept source OCT). In the so-called time domain OCT mode, in which the path length of the reference beam is buried during the measurement, the OCT detector 3 may likewise consist of a point detector.

Collinearly with the OCT measurement beam, there is an imaging beam path for video recording. The imaging beam path (for visible and infrared light) is, for example, coupled in through semitransparent mirrors 11. It consists of an illumination beam 6a and an observation beam path 6b. Illumination 7 is, for example, generated by an LED in the visible or infrared wavelength range. The reflected light 6b strikes a light-sensitive sensor 8, for example a CCD chip, through imaging optics 2. The image information of the CCD chip is on the one hand visualized directly on a monitor 9, and on the other hand the image is stored digitally on a data medium in a control computer 10.

Figure 2:
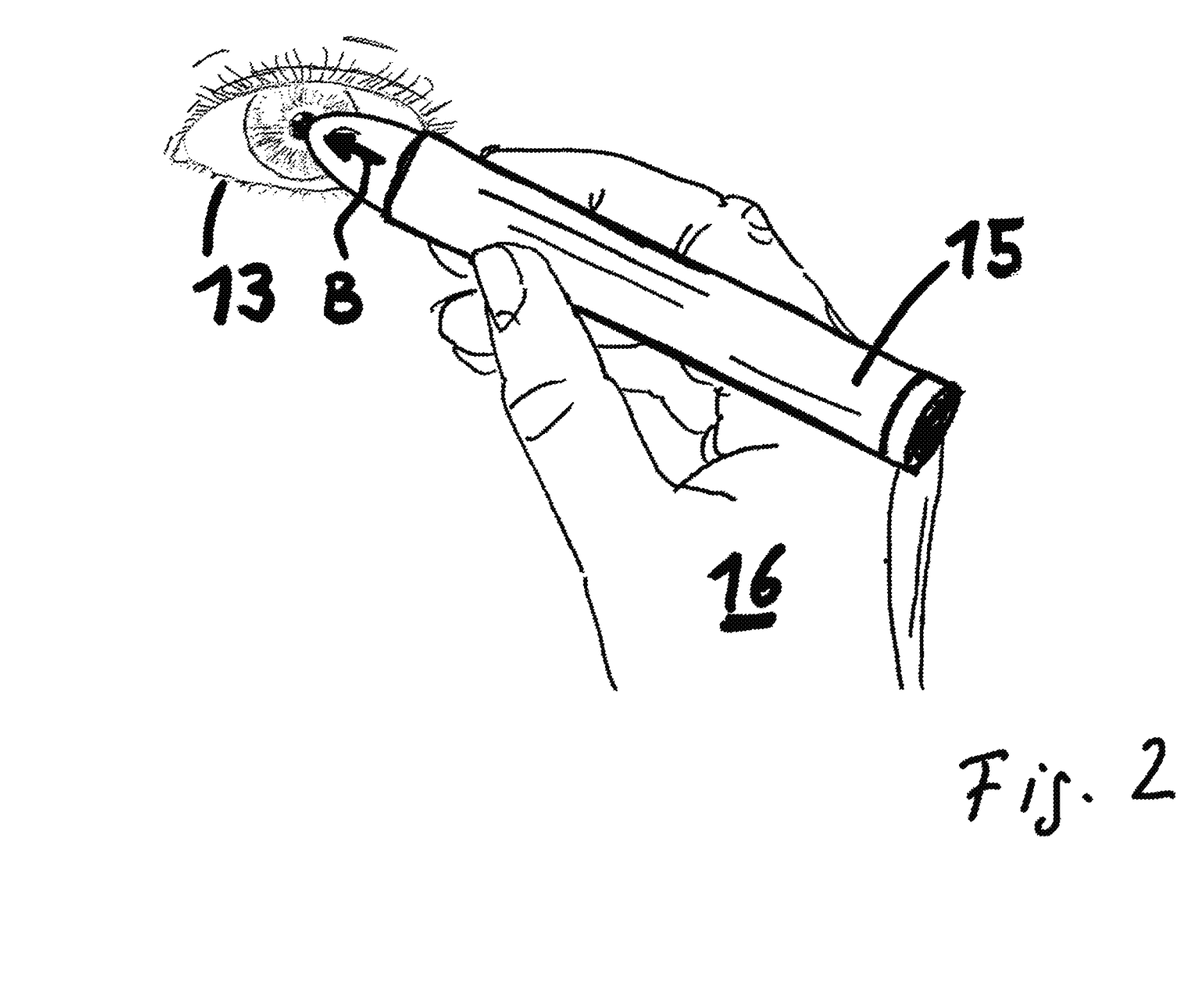
FIG. 2 is a perspective view of a first exemplary embodiment of the invention during use.

If, for example, the OCT device is placed on the cornea 12 of the eye 13, the imaging beam path is designed in such a way that a small section of the retina 14 of the eye 13 can be represented thereby. Movement of the arrangement 15 relative to the eye 13, for instance by tilting or lateral displacement by the hand of the examiner 16, illuminates a new area of the retina 14 and correspondingly represents this image on the monitor and stores the information at a sufficiently rapid cycle rate on the data medium in the control computer 10.

This process is systematically comparable approximately to searching for a surface concealed in darkness with a searchlight. If the illuminated area is remembered, an arbitrarily large composed image of the searched—scanned—surface is obtained.

Simultaneously with the freehand scanning of the retina surface by the imaging beam path, a depth profile of the retina 14 is produced by means of an OCT measurement beam at the center of the illuminated area, or video section. The OCT measurement beam in this case penetrates into the position to be measured on the cornea 12 (or another subject), and a part of the OCT radiation is reflected or scattered back to the detector. The backscattered OCT radiation is superimposed interferometrically with a reference beam. This gives rise to individual axial interferograms. A single interferogram (optical cross-correlation) of a reference beam and measurement beam gives a linear pattern that images the strength of the light-reflecting structures and their relative optical path length as an axial depth profile (A-scan or amplitude-mode scan). By moving the arrangement, the measurement beam is then guided transversely over the surface of the retina, so that a flat tomogram (B scan or brightness-mode scan) or even a three-dimensional volume (c-mode scan) may be recorded by scanning.

Figure 3A:
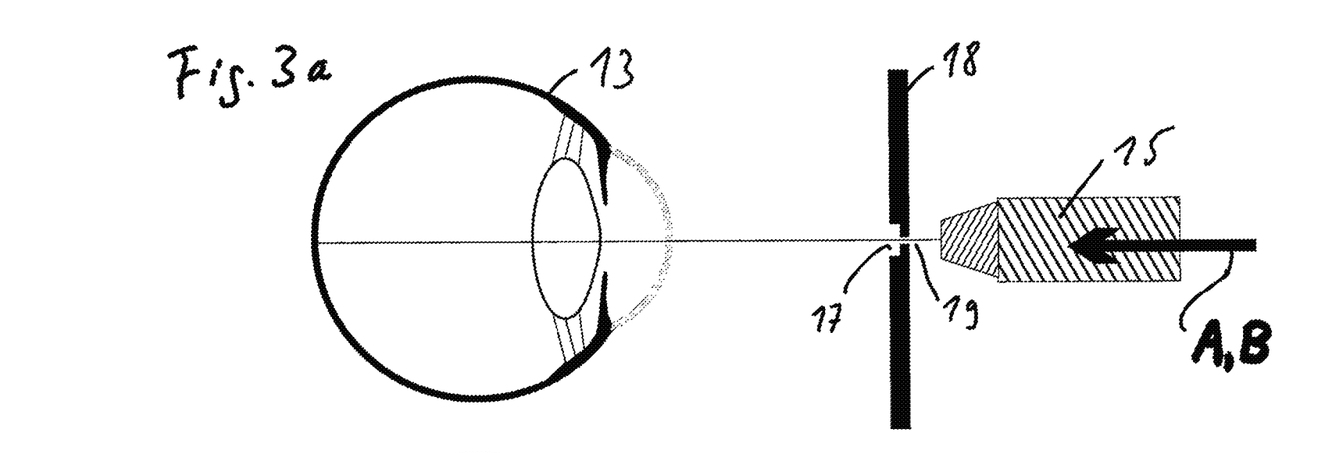
FIGS. 3a and 3b are schematic views of a second exemplary embodiment of the invention, in which the patient is requested to follow a moving fixation light with his eye (the fixation light may be generated and moved by a screen inside an arrangement)
Figure 3B:
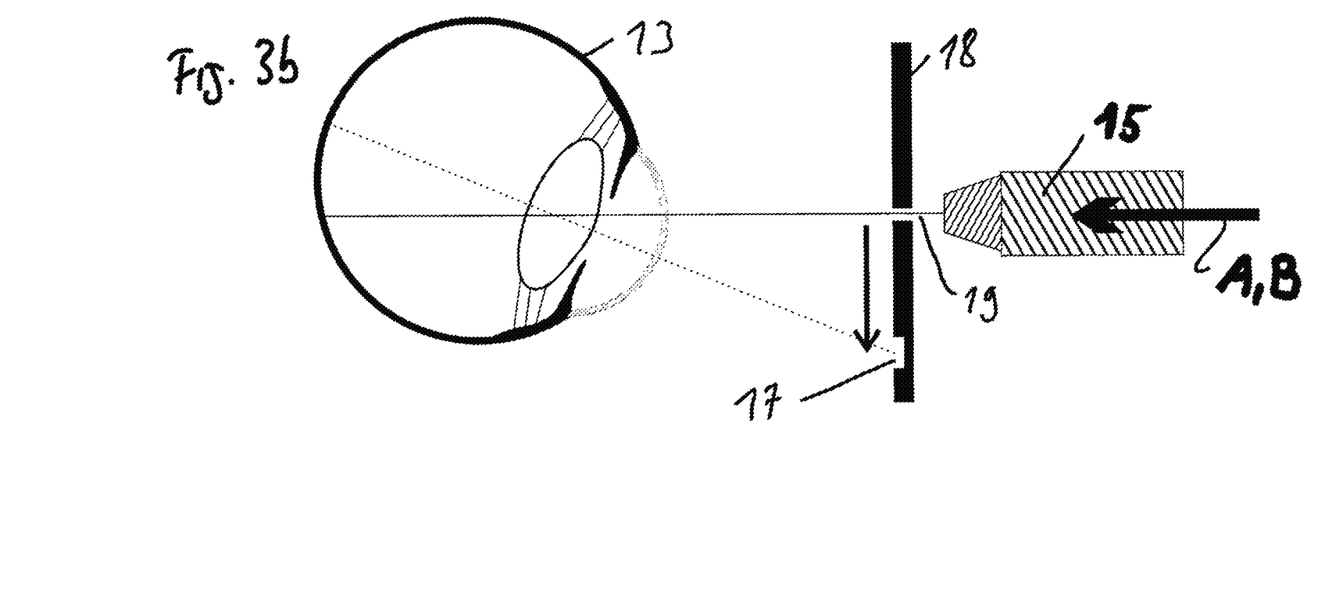

As an alternative to moving the OCT device 15, and as shown in FIGS. 3a and 3b, in another embodiment, with the OCT device static, the patient may be requested to follow a moving fixation light 17 with his eye 13. The fixation light 17 may be generated by a screen inside the arrangement and moved on the screen. The measurement beam 5, the backscattered light 5 and the imaging beam path 6a, 6b may pass through a central opening 19 onto the eye 13 and back again into the measuring arrangement 15. By the movement of the patient's eye, a scan of the retina 14 is likewise formed.

Since the freehand movement of the described arrangement (or the movement of the eye) and, therefore, the scanning over the retina 14 often takes place with insufficient definition or reproducibility, it is advantageous for the resulting two-dimensional photographic surface images of the retina 14, as well as the individual axial depth profiles to be subsequently combined by software in the control apparatus ("stitching").

Figure 4A:
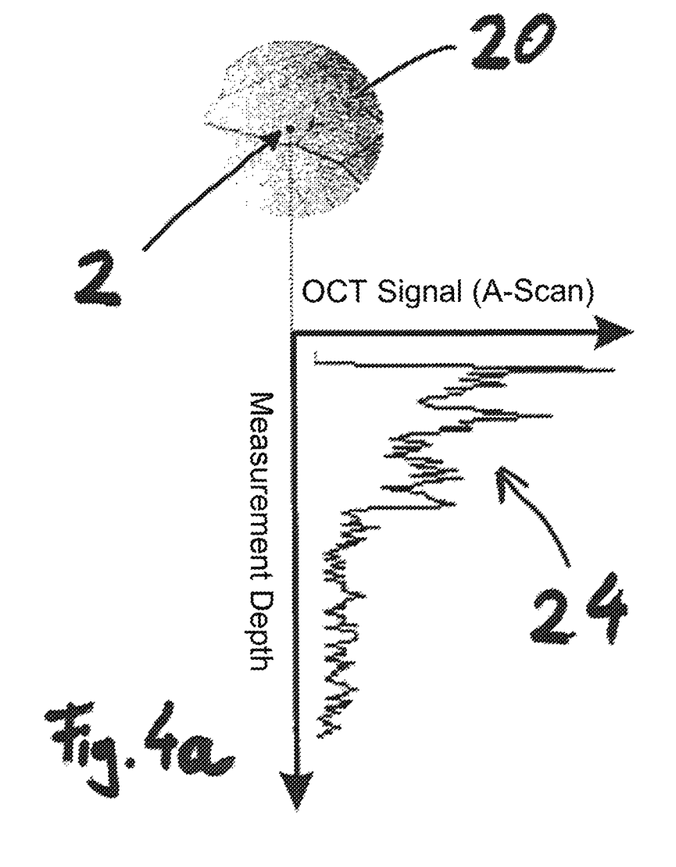
FIG. 4a is a view of an exemplary representation of a first measurement result of the OCT device according to the invention as a single video image with central marking of the OCT measurement point, and an A-scan associated therewith.
Figure 4B:
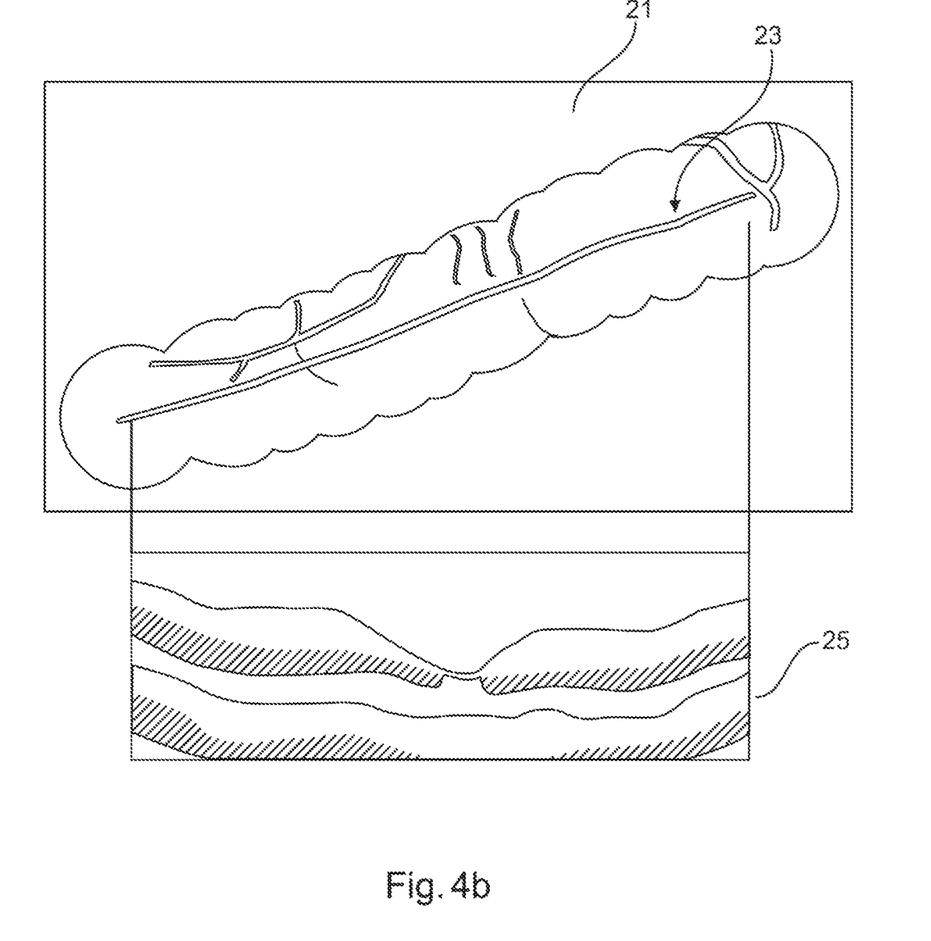
FIG. 4b is a view of an exemplary representation of a second measurement result of the OCT device according to the invention with sequenced video images, a resulting line of the OCT measurement points, and an associated B-scan.

With the aid of the control computer 10, to this end the individually recorded video surface recordings 20 are transferred into a virtual coordinate system and finally combined to form an overall image 21. The position of the OCT measurement beam may be marked as a point 22 in each individual surface recording. According to the movement of the arrangement, one or more continuous lines 23 on the overall recording 21 are obtained from the individual marking points. Synchronously with the recorded line, each individual depth scan of the OCT measurement (A-scan) 24 along the line may be plotted graphically in order to obtain a corresponding two-dimensional tomogram (B-scan) 25.

The combining of the individual images 20 of the surface to form an overall image 21 is carried out in such a way that an overlap of two adjacent images in the respectively matching image sections is maximized, and optionally the individual images are rectified for a congruent overlap.

In addition, a plurality of, for example three, sensors 30 are fitted in the arrangement which register and record the movement of the arrangement in all three spatial directions. This may simplify the combining of the individual images and make it more precise. Such sensors 30 may, for example, be acceleration sensors which register translational and/or rotational movements or register the orientation of the arrangement in relation to up and down by means of gravity. Gyroscopes may likewise be used as sensors 30 in order to register and track movements of the measuring arrangement. With the aid of these sensors, the orientation of the OCT measurement beam and of the imaging beam path may be determined at any instant within the recording period of the scan. With the aid of the orientation determined in this way, the recorded images may then be combined to form an overall image and the recorded OCT measurement profiles may then be combined on an overall measurement profile.

The invention claimed is:

1. An OCT examination device for recording an object by optical coherence tomography comprising:
    an OCT radiation source emitting OCT radiation with a wavelength of 400 nm to 2000 nm and a spectral bandwidth within at least a range of 20 nm to 400 nm or a narrow bandwidth of less than 20 nm to 400 nm, the radiation source being tunable such that the narrow bandwidth forms a wider bandwidth of 20 nm to 400 nm by time-offset emission of waves at different wavelengths;
    an OCT beam path comprising an OCT output direction of the OCT radiation from the OCT radiation source and an OCT input direction of backscattered OCT radiation scattered back by the object;
    an OCT radiation receiver for receiving the backscattered OCT radiation;
    a housing containing the OCT radiation source and the OCT radiation receiver,
    an exit opening formed in the housing for the OCT radiation of the OCT radiation source;
    an entry opening formed in the housing for the backscattered OCT radiation;
    an OCT exit direction of the radiation through the exit opening;
    an OCT entry direction of the backscattered OCT radiation through the entry opening;
    a fixation light generated by a screen inside the OCT examination device and moved on the screen such that a patient follows the moving fixation light with an eye of the patient during a measurement such that by a movement of the eye of the patient a scan of a retina of the eye of the patient is formed; and a control unit in signal communication with the OCT radiation source and the OCT radiation receiver and configured to record a multiplicity of measurement profiles mutually separated in a recording period and, within the recording period, to drive the OCT radiation source in order to emit the OCT radiation and the OCT radiation receiver to receive the backscattered OCT radiation;

wherein the OCT output direction and the OCT exit direction are kept constant with respect to one another in their angular orientation during the recording period.

2. The OCT examination device as claimed in claim 1, wherein the entry opening and the exit opening are formed by a single housing opening.

3. The OCT examination device as claimed in claim 1, wherein the exit opening and the OCT radiation source are arranged such that the OCT exit direction and the OCT output direction extend parallel to one another.

4. The OCT examination device as claimed in claim 3, wherein the exit opening and the OCT radiation source extend in coaxial relation to one another.

5. The OCT examination device as claimed in claim 1, further comprising an observation instrument comprising:
   an illumination radiation source emitting light in the visible or infrared observation wave range into an illumination beam path passing through the exit opening; and
   an observation image sensor sensitive to radiation in the visible or infrared observation wave range and which receives a reflected light in the visible or infrared observation wave range from an observation beam path passing through the entry opening;
   wherein the observation beam path and the OCT exit direction extend parallel to one another.

6. The OCT examination device as claimed in claim 5, wherein the observation beam path and the OCT exit direction extend in coaxial relation to one another.

7. The OCT examination device as claimed in claim 5, wherein the electronic control unit comprises an image processing unit configured to combine a first image formed by the reflected light received by the observation image sensor, and a second image, adjacent to the first image and formed with a time offset with respect to the first image, from the reflected light received by the observation image sensor to form an overall image.

8. The OCT examination device as claimed in claim 7, wherein the image processing unit is configured to identify an intersection region of the first and second images, in which a matching image section is reproduced in the first and second images, and to combine the first and second images such that the overall image is composed of the first and second image with an overlap of the first and second images in the matching image section.

9. The OCT examination device as claimed in claim 7, wherein the image processing unit is configured in order to rectify the first or the second image by the first or the second image being tilted about an image surface normal as a tilt axis.

10. The OCT examination device as claimed in claim 7, wherein the image processing unit is configured in order to rectify the first or the second image by the first or the second image being scaled in all regions with a matching scaling factor or with a scaling factor decreasing in one or two mutually perpendicular spatial directions.

11. The OCT examination device as claimed in claim 7, wherein the control unit is configured to process a measurement profile, compiled from the backscattered OCT radiation received by the OCT radiation receiver and an image recorded simultaneously from the reflected light received by the observation image sensor, and to mark a region in the image which represents the position of the measurement profile.

12. The OCT examination device as claimed in claim 1, wherein the OCT radiation source and the OCT radiation receiver are arranged immovably in the housing.

13. The OCT examination device as claimed in claim 1, wherein the OCT beam path extends immovably in the housing.

14. The OCT examination device as claimed in claim 5, wherein the OCT beam path is static in relation to the illumination beam path and the observation beam path.

15. The OCT examination device as claimed in claim 1, further comprising:
   a placement recording unit configured to determine a placement of the OCT radiation receiver; and
   an image processing unit in signal communication with the placement recording unit, wherein the image processing unit is configured to:
   determine a first measurement profile of the backscattered OCT radiation received by the OCT radiation receiver at a first instant;
   determine a first placement of the OCT radiation receiver at the instant of receiving the backscattered OCT radiation of the first measurement profile from placement data transmitted from the placement recording unit at the first instant to the image processing unit;
   determine a second measurement profile, adjacent to the first measurement profile with a time offset with respect to this first measurement profile, from the backscattered OCT radiation received by the OCT radiation receiver at a second instant;
   determine a second placement of the OCT radiation receiver at the instant of receiving of the backscattered OCT radiation of the second measurement profile from placement data transmitted from the placement recording unit at the second instant to the image processing unit;
   determine the relative placement of the first measurement profile with respect to the second measurement profile with the aid of the first and second placements; and
   combine the first and second measurement profiles to form an overall measurement profile by entering the first and second measurement profiles into the overall measurement profile at the previously determined relative placement.

16. The OCT examination device as claimed in claim 15, wherein the placement of the OCT radiation receiver is determined by the position or the orientation of the OCT radiation receiver in relation to a static reference coordinate system.

17. A method for OCT image capture of an object by optical coherence tomography using an OCT examination device, the method comprising the steps of:
   emitting OCT radiation from an OCT radiation source into an OCT beam path, the OCT radiation having a wavelength of 400 nm to 2000 nm and a spectral bandwidth that comprises at least a range of 20 nm to 400 nm or has a narrow bandwidth of less than 20 nm to 400 nm, the radiation source being tunable in such that the narrow bandwidth forms a wider bandwidth of 20 nm to 400 nm by time-offset emission of waves at different wavelengths, wherein OCT examination device comprises:

an OCT output direction of the OCT radiation from the OCT radiation source;

an OCT input direction of backscattered OCT radiation scattered back by an object;

a housing comprising an exit opening and an entry opening for an OCT beam path, the housing containing the OCT radiation source and an OCT radiation receiver; and a fixation light generated by a screen inside the OCT examination device and moved on the screen such that a patient follows the moving fixation light with an eye of the patient during a measurement such that by a movement of the eye of the patient a scan of a retina of the eye of the patient is formed;

receiving the backscattered OCT radiation of the OCT radiation source by the OCT radiation receiver;

guiding the OCT radiation through the exit opening in an OCT exit direction;

guiding the backscattered OCT radiation through the entry opening in an OCT entry direction;

driving the OCT radiation source and the OCT radiation receiver by a control unit in order to emit the OCT radiation from the OCT radiation source and to receive the backscattered OCT radiation by the OCT radiation receiver over a recording period; and recording a plurality of mutually separated measurement profiles from the backscattered OCT radiation during the recording period;

wherein the OCT output direction and the OCT exit direction are kept constant with respect to one another in their angular orientation during the recording period.

18. The method for OCT image capture as claimed in claim 17, wherein the plurality of mutually separated measurement profiles from the backscattered OCT radiation during the recording period includes a recording of a first image and a recording of a second image, and wherein OCT observation image sensor is displaced or tilted relative to the object between the recording of the first image and the recording of the second image.

19. The method for OCT image capture as claimed in claim 17, wherein a first measurement profile and a second measurement profile are recorded within the recording period, and the first and second measurement profiles are assigned to one another in their spatial placement and combined to form an overall measurement profile by:

simultaneously with the recording of the first measurement profile, a first image being recorded by emitting light radiation in the visible or infrared wavelength range and receiving the light reflected by the object;

simultaneously with the recording of the second measurement profile, a second image being recorded by emitting light radiation in the visible or infrared wavelength range and receiving the light reflected by the object;

the position of the first measurement profile in the first image being marked;

the position of the second measurement profile in the second image being marked;

the first and second images being combined with the aid of image analysis to form an overall image by a matching image region of the first and second images being arranged in an overlapping manner; and the relative positioning of the first measurement profile with respect to the second measurement profile being determined with the aid of their position in the overall image, and the first and second measurement profiles being combined with the aid of the relative positioning determined in this way to form an overall measurement profile.

20. The method for OCT image capture as claimed in claim 17, wherein a first measurement profile and a second measurement profile are recorded within the recording period, and the first and second measurement profiles are assigned to one another in their spatial placement and combined to form an overall measurement profile by:

a first placement of the housing being recorded simultaneously with the recording of the first measurement profile;

a second placement of the housing being recorded simultaneously with the recording of the second measurement profile; and the relative positioning of the first measurement profile with respect to the second measurement profile being determined with the aid of a relative change in the first placement with respect to the second placement of the housing, and the first and second measurement profiles being combined with the aid of the relative positioning determined to form an overall measurement profile.

* * * * *